United States Patent [19]

Amirav et al.

[11] Patent Number: 5,686,656
[45] Date of Patent: Nov. 11, 1997

[54] METHOD AND DEVICE FOR THE INTRODUCTION OF A SAMPLE INTO A GAS CHROMATOGRAPH

[75] Inventors: Aviv Amirav, 58 Bialik Avenue, Ramat Hasharon 47205; Shai Dagan, Ramat Gan, both of Israel

[73] Assignee: Aviv Amirav, Hasharon, Israel

[21] Appl. No.: 607,474

[22] Filed: Feb. 27, 1996

[51] Int. Cl.[6] .................................................. G01N 30/02
[52] U.S. Cl. .......................................................... 73/23.41
[58] Field of Search ............................ 73/23.35, 23.37, 73/23.41, 23.42, 863.11, 863.12, 864.81; 250/288, 282; 96/105

[56] References Cited

U.S. PATENT DOCUMENTS

| | | | |
|---|---|---|---|
| 4,035,168 | 7/1977 | Jennings | 73/23.35 |
| 4,162,977 | 7/1979 | Guillemin et al. | 96/105 |
| 4,213,326 | 7/1980 | Brodasky | 73/23.1 |
| 4,245,494 | 1/1981 | Legendre et al. | 73/23.37 |
| 4,422,860 | 12/1983 | Feinstein | 96/105 X |
| 4,440,550 | 4/1984 | Jenkins et al. | 96/105 X |
| 4,470,315 | 9/1984 | Ellgehausen et al. | 73/863.12 |
| 4,474,588 | 10/1984 | Hinshaw | 96/105 |
| 4,559,063 | 12/1985 | Munari et al. | 96/105 X |
| 4,594,506 | 6/1986 | Ghaderi | 250/288 |
| 4,615,226 | 10/1986 | DiNuzzo et al. | 73/863.11 |
| 4,711,764 | 12/1987 | Good | 96/105 X |
| 4,713,963 | 12/1987 | Sharp | 73/23.37 X |
| 4,732,046 | 3/1988 | Lawrence et al. | 73/863.12 |
| 5,055,677 | 10/1991 | Amirav et al. | 250/282 |
| 5,065,614 | 11/1991 | Hartman et al. | 73/23.35 |
| 5,281,397 | 1/1994 | Ligon et al. | 73/23.37 X |
| 5,472,670 | 12/1995 | Harrington et al. | 73/23.42 X |

Primary Examiner—Michael Brock
Assistant Examiner—Jay L. Politzer
Attorney, Agent, or Firm—McAulay Fisher Nissen Goldberg & Kiel, LLP

[57] ABSTRACT

There is provided a method for sample introduction into a gas chromatograph for performing sample analysis, in which a sample is introduced into a removable sample container, the container is placed in a sample introduction device, the device with said container is inserted into a gas chromatograph injector, and the sample is then vaporized for effecting analysis thereof by the gas chromatograph. The non-volatile residues of the sample retained in the container after vaporization and are removed with the container prior to performing the next analysis. There is also provided a method for direct sample introduction into a mass spectrometer for performing sample analysis, in which a sample is loaded into a sample container, the container with the sample is introduced into the injector of a gas chromatograph connected to a mass spectrometer through a capillary column, the injector is heated to a temperature sufficient to vaporize the sample to produce a flow of compounds which are swept to the mass spectrometer by a carrier gas, and the container is removed from the injector prior to performing the next analysis. Devices for introducing samples into a gas chromatograph for analyzing said sample are also described and claimed.

42 Claims, 11 Drawing Sheets

METHOD AND DEVICE FOR THE INTRODUCTION OF A SAMPLE INTO A GAS CHROMATOGRAPH

BACKGROUND OF THE INVENTION

The present invention relates to a method and device for the introduction of a sample into a gas chromatograph for effecting sample analysis.

DESCRIPTION OF THE PRIOR ART

Gas chromatography is one of the most popular methods for sample analysis. A gas chromatography apparatus includes a sample injector for sample thermal vaporization and transfer into the separation column, a separation column in a temperature-controlled oven and a suitable detector to record the amount and time of appearance of the anlayzed compounds. The sample compound mixture is separated in time and each compound is identified by its time of elution. The gas chromatograph can also be coupled with a mass spectrometer that acts as its detector for improved sample identification capability through the provision of its compound specific mass spectrum.

Traditionally, samples are introduced into the gas chromatograph (GC) through their injection from a small syringe that penetrates a septum and dispenses a measured amount of liquid sample into the GC injector for vaporization and further transport through sweeping by a carrier gas into the separation column. Usually, the injection is into a glass liner that is characterized by a clean and deactivated surface area to ensure a quantitative sample transfer.

The majority of samples that require analysis, however, are in a natural form that cannot be directly introduced as is into the GC. Typical examples include biofluids such as blood or urine that should be analyzed for the presence of trace level of drugs, or food items such as fruit, vegetables and meat that need to be monitored for the presence of harmful pesticides at low levels. The food items above are solids and cannot be quantitatively introduced into the GC. This problem can easily be overcome by blending the food items with a suitable solvent such as acetone. After this liquification procedure, there is obtained what is denoted as "sludge", i.e., a thick, rich mixture that contains a large portion of dirt. All these samples and many others cannot be injected as is into the GC, since only a portion thereof will be vaporized and the rest will be deposited as a solid salt (urine), coagulated solid (blood) or carburized organic fibers and residue (food items). These residues quickly plug the GC injector and column, and moreover, certain slightly volatile compounds slowly migrate from the GC liner into the beginning of the column and tend to poison its activity and act as trapping sites for trace levels of the analytes. Accordingly, it is a common practice to process the sample and bring it to the form that is compatible with the requirements of GC injection. Traditionally, the major sample preparation and clean-up methods used involve liquid-liquid sample extraction, but recently solid phase extraction methods are also being used. All these sample preparation methods are expensive, labour intensive, time consuming and liable to large errors due to large variability of the extraction efficiency between different analytes. It is commonly accepted that sample preparation is the most time consuming element and bottleneck of the whole analysis procedure.

An important additional tool for sample analysis is the mass spectrometer (MS). It is based on sample introduction and vaporization in an ion source, followed by molecular ionization. The ions are further transferred into a mass analyzer that separates them according to their mass, and the detected ions produce a very characteristic mass spectrum that is very effective in sample identification through the molecular weight and fragment weight information. The mass spectrometry analysis can also be applied to simple mixtures, since different compounds can have different characteristic mass peaks. This type of analysis can become even more specific by the use of mass spectrometry-mass spectrometry (MS—MS), where the chosen mass ion is collisionally activated to produce daughter ion mass spectrum. The mass spectrometer can also be combined with a gas chromatograph to form a GC-MS apparatus that is especially effective in complex mixture analysis, due to the combination of time and mass separations. Thus, most mass spectrometers today contain a GC as their sample inlet system and a growing number of GCs contain an MS as their detector. Traditionally, the sample is introduced to the mass spectrometer either from a GC whose column ends at the MS ion source, or through the use of a direct sample introduction (insertion) (DSI) device that brings the unseparated row sample in a disposable vial or test tube directly into the ion source and controls its vaporization temperature. The use of a GC for sampling is slow and typically takes more than 30 minutes. The sample also spends only a few seconds in the ion source, which is too short for the study of the parameters that affect the sample mass spectrum. The GC sampling is also limited in its ability to deliver relatively non-volatile and thermally labile compounds that decompose in the GC column or in the injector. The conventional DSI, on the other hand, requires a special air lock chamber and by-pass pumping system for the transfer of the sample container from the room atmosphere into the ion source vacuum chamber. It also requires a special transfer mechanism and a separate sample heating system to control the vaporization rate inside the ion source. Overall, although effective, the DSI is a complex and costly device. Moreover, once used, in many cases a too large amount of sample is vaporized directly onto the ion source, requiring a long cleaning time before switching into a GC-MS operation is possible. In addition, direct solvent introduction is hard as these solvents immediately boil vigorously and splash inside the vacuum system before entering the ion source. Thus, solids must be introduced as powders and not as liquid solutions.

SUMMARY OF THE INVENTION

It is therefore a broad object of the present invention to provide a method and device for direct sample introduction into a gas chromatograph.

It is a further object of the present invention to provide a method for direct introduction into a gas chromatograph of sludge and other dirty samples by way of injection into a GC that will overcome the many disadvantages and limitations described hereinbefore.

The invention incorporates novel methods and devices facilitating the introduction of samples into the GC injector in a removable sample container instead of being dispensed as a liquid from a syringe. Accordingly, the dirt and non-volatile harmful material residues remain in the sample container and can be removed before the next analysis, thus enabling the analysis of sludge and dirty samples without prior clean-up and extraction. Alternatively, the GC injector temperature can be adjusted to provide a constant vaporization rate of the sample compound from its container, that can be used for its study or analysis by mass spectrometry or other GC detectors.

According to the present invention, there is provided a method for sample introduction into a gas chromatograph for performing sample analysis, comprising introducing a sample into a removable sample container; placing said container in a sample introduction device; inserting said device with said container into a gas chromatograph injector; vaporizing the sample for effecting analysis of said sample by the gas chromatograph while causing non-volatile residues of said sample to be retained in said container, and removing said container with said residues prior to performing the next analysis.

The invention also provides a method for direct sample introduction into a mass spectrometer for performing sample analysis, comprising loading a sample into a sample container; introducing said sample container into the injector of a gas chromatograph connected to a mass spectrometer through a capillary column; heating said injector to a temperature sufficient to vaporize said sample to produce a flow of compounds which are swept to the mass spectrometer by means of a carrier gas, and removing said container from said injector prior to performing the next analysis.

The invention further provides a device for sample introduction into a gas chromatograph for analyzing said sample, comprising means for coupling a sample introduction device having means for carrying a removable sample container into a gas chromatograph injector and means for sealing the sample introduction device and said means for coupling to each other.

The invention still further provides a device for sample introduction into a gas chromatograph for analyzing a sample, comprising a needle-less syringe-like means for pumping a measurable amount of sample; means for coupling and removing an open-ended capillary; a capillary sample container for the introduction of said sample into the gas chromatograph injector, and means for retaining said sample in its container while being inserted into the gas chromatograph injector.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DESCRIPTION OF THE PREFERRED EMBODIMENTS

Figure 1:
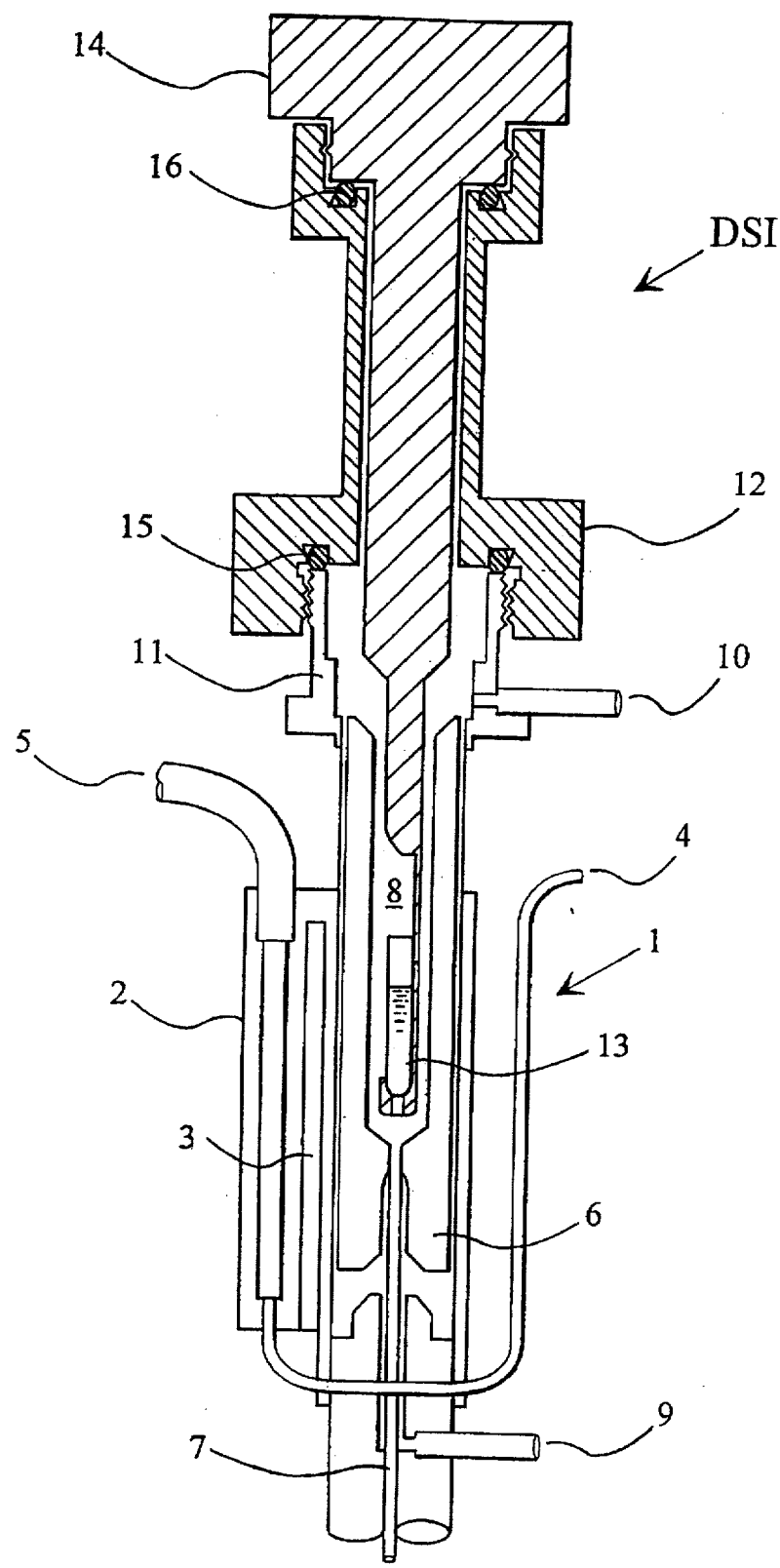
FIG. 1 is a partial cross-sectional and plan view of a direct sample introduction device according to the present invention, as coupled to a standard GC injector.

In FIG. 1 there is illustrated a schematic diagram of a Direct Sample Introduction Device (DSI) mounted on a standard commercially available GC injector that can be temperature programmed. The elements of the existing GC injector 1 include a fast heating block 2 with its temperature probe 3 and coolant (air, $CO_2$ or liquid nitrogen) entrance 4 and exit 5. The injector 1 includes a glass liner 6 that accepts the analytical column 7 at its lower end and is designed to accept a sample introduction device at its upper end volume 8. The GC carrier gas is introduced from inlet 9 and enters into the column 7, or can exit at a low flow rate from the septum purge exit 10 or from a split exit (not shown) in split splitless injectors. The injector 1 also contains a septum holder or seat 11 without a septum, which is removed to allow the insertion of the DSI device. The original septum cover (not shown) was also removed and replaced by the DSI device coupling element 12. The sample is introduced into a removable sample container 13, which, in the shown embodiment, is a small test tube (vial) with typical dimensions of 1.6 mm OD, 1.2 mm ID and 15 mm long, made out of pyrex glass.

The sample container 13 is carried by the sample container holder 14, designed for easy and fast insertion and removal of the sample container. The DSI device coupling element 12 is sealed with a VITON® (is a registered trademark owned by E.I. DuPont De Nemours ad Company for synthetic rubber and rubber compositions.) O-ring 15 (KALREZ® for high temperatures), and similarly, the sample holder 14 is also sealed with an O-ring 16 Kalrez is a registered trademark owned by E.I. DuPont De Nemours and Company for precision parts made of perfluoroelastomers.

Typical operation of this DSI for dirty sample introduction for GC or GC-MS analysis is performed in the following steps:

1. The injector 1 and analytical column 7 are cooled to a suitable low temperature at the end of a previous analysis.

2. The sample holder 14 is removed and a low protective helium flow is released from the injector to avoid the penetration of air.

3. The previous sample container 13 is removed.

4. A new, measured volume sample is loaded into a new sample container.

5. The container is inserted into the sample holder 14.

6. The sample holder 14 with the sample container 13 are introduced into the GC injector 1 inside its liner 6, as shown in FIG. 1.

7. The GC is activated.

8. The GC injector temperature is maintained at a relatively low value above the solvent boiling temperature, or is raised in a pretested programmed fashion to allow the gentle vaporization of typically 0.5–5 microliters solvent in the sample container. The temperature is further automatically increased to a predetermined value for volatile compounds vaporization and then, typically after about up to 1 minute, the injector temperature is reduced to eliminate any further vaporization of less or non-volatile compounds.

9. Vaporized compounds are trapped at the beginning of the analytical column, as usually encountered with conventional syringe-based injections, since the column oven temperature is adjusted to a relatively low value for the effective trapping of the semi-volatile organic compounds.

10. After a predetermined amount of time, the GC oven temperature is raised according to a predetermined temperature program and the GC analysis is performed in the usual way.

11. The carrier gas flow rate through the injector and column is an important parameter to optimize. A flow restriction element must be provided to limit the maximum flow rate to the room during the sample loading step, that involves a temporarily open injector. The limited carrier gas flow rate acts as a purge gas to protect against air penetration to the column, that is maintained at a protective relatively low temperature during the sample loading. A higher efficiency thermal extraction (vaporization) from the removable sample container can be achieved at a relatively high flow rate of 5–20 ml/min during the vaporization period. It might be reduced to a lower optimal column flow rate during the GC temperature program. The injection split flow can also be open during the solvent vaporization stage, to speed it up.

This new approach can be used with all the GC analytical columns, but its use with open tubular capillary columns is especially effective. This is due to the good cyro-trapping and high temperature range of capillary columns, as well as their higher sensitivity and vulnerability to poisoning by impurities combined with their higher price. These columns are also characterized by much lower sample capacity and carrier gas flow rate that make this method especially challenging in terms of fitting to smaller injector liners that are optimized for capillary columns.

It is to be emphasized that the present design as shown in FIG. 1 was specifically optimized for the handling of liquid or liquified samples. The majority of samples are naturally liquids, including drinking water, urine, blood, milk, juice, oil, etc., while others are liquified solids such as blended fruit, vegetables, meat, etc. There are several compelling reasons for the tendency to liquify solid samples for their GC analysis, including:

1. Blending with a solvent, such as acetone, induces an effective extraction of the analyzed compounds from the bulk of the solid. This is the case in the analysis of pesticides in food.

2. Liquids are much easier to quantitatively and precisely measure with a syringe, simply by measuring their volume. Syringe-based dispensing is also much more reproducible than weighing and can be automated. Standard capillary GC compatible sample size is 1 µL, whose weight is only 1 milligram, which is hard to handle and weigh as a solid sample.

3. The current GC technology today is based on liquid (or gas) injections.

On the other hand, liquids present problems of dripping and wetting of surfaces and can also splash or form sprays. Thus, the DSI shown in FIG. 1 is structured to hold a removable sample container with its mouth directed upward, so that the liquid will not drop down by the force of gravity. In addition, the length of the sample container is long enough to enable gentle solvent vaporization with effective trapping of the relatively non-volatile residues.

According to the present invention, the sample is loaded in a removable small sample container. The embodiment of a separate sample container and its holder enables the sample container to be made from a low cost, small size, inert glass container that can be disposed after use. On the other hand, the removable sample container holder is configured to be robust and is made from a strong non-breakable material such as stainless steel with a passivated surface to enable robust, repetitive sample loading in a manual or automated way.

While the DSI is adopted for opimized "dirty" liquid handling, it is also effective in the solvent-free sampling of solids and powders. This is the result of the small size and weight of the removable sample container that enables accurate weighing of the solid sample and the vertical position of the sample vial that protects the sample from falling down.

When a direct sample introduction into a mass spectrometer is performed, a relatively pure sample is introduced into the sample container and the injector temperature is maintained at a value that results in a constant useful vaporization rate of the anlayzed compound, that produces the required sample molecular flux at the mass spectrometer ion source. In this case, in order to minimize the equilibration and response time, a short capillary column with 1–2 meter length is used, preferably with a very thin or no adsorption layer coating, and the GC oven and transfer line to the mass spectrometer are held at a high temperature to ensure fast response. The vaporized sample quickly flows with the carrier gas to the mass spectrometer ion source, where it is ionized and mass analyzed in the normal way, for sample analysis or for the study of the sample mass spectrum. The DSI coupling element 12 can be easily removed and the GC injector can be converted back to normal syringe-based liquid dispensing injection in a short time.

With standard bench top GC-MS instrumentation, a short microbore capillary column is desirable to minimize the gas load on the MS during normal GC-MS operation with a second standard analytical column.

Although very simple in its appearance and applications, this novel direct sample introduction device and method of operation have several important advantages over the existing methods and devices, both in dirty sample analysis as well as in direct sample introduction into a mass spectrometer.

The same direct sample introduction device that brings a sample in a removable sample container into a GC injector, can be used for two different applications of sample introduction for GC analysis and sample introduction to a mass spectrometer for mass spectrometric analysis or studies. Each of these methods has several important advantages.

A. Direct Sample Introduction into a Mass Spectrometer

The following are the advantages of the present novel approach over the conventional air-lock and by-pass pumping assembly.

The DSI through the GC injector method is simpler and thus costs much less to produce, since a second GC injector already exists in most GC-MS systems and the use of the costly air lock chamber, by-pass pumping system and rotary pump is eliminated.

The DSI through the GC injector is much faster and easier to operate, due to the elimination of the by-pass pumping step.

The DSI through the GC can also accept dilute solvents, in contrast to the conventional DSI method, since the vaporization of solvents under 1–3 atmospheres can be very gentle without splashing into the vacuum system. This feature is translated into the ability to simplify the introduction of powders through their solvation in common solvents and introduction with a syringe into a small vial. The usual requirement of solvent drying is also avoided in the analysis of chemical reaction products in their original solution, etc.

The DSI through the GC is much cleaner, easier and faster to switch from sample to sample, since the GC injector is built with ultra-clean materials of deactivated glass, as it is designed for fast cleaning. This is in marked contrast to MS ion sources that are optimized for ionization and thus are built from metals. The GC injector can be quickly heated under high carrier gas flow rates for even faster cleaning.

The DSI through the GC injector can be interchanged with GC-MS analysis very quickly in contrast to conventional DSI. In practice, two columns can be connected to the MS ion source, one from the DSI-GC injector and one from a GC injector coupled with a standard GC column. The fast cooling of the DSI-GC injector and the reduction of its flow rate can practically eliminate its effect on the MS ion source and allow immediate GC-MS analysis even without DSI-GC injector cleaning and even without the removal of the DSI sample container.

The DSI through the GC injector can serve for on-line, separately optimized sample introduction into the MS ion source during GC-MS analysis. This procedure may be used in several applications, including:

a. introduction of a liquid (or solid) compound for serving as a chemical ionization (CI) agent;

b. introduction of heavy water or deuterated methanol for the exchange of labile hydrogen atoms in OH, NH groups with deuterium for their identification;

c. special relatively non-volatile high mass compounds can be constantly introduced for on-line accurate mass calibration, required to eliminate mass drifts when ultra-high mass resolution and high mass calibration are required.

The ability to provide liquid chemical ionization (CI) and deuterating agents is very appealing to eliminate the conventional bulky and costly gas cylinders and their pressure regulators and gas lines.

The DSI through the GC injector enables the application of selective chemical reactions such as oxidation, that requires approximately one atmospheric pressure or solution derivatization.

The method of DSI through the GC injector can be applied to all the existing GC-MS instruments with very little hardware changes. This is in marked contrast to the conventional DSI devices that practically cannot be "field" implementated in existing GC-MS systems.

The same DSI mentioned above can also be used for dirty sample injection into the GC column for its standard GC-MS analysis. Thus, the dual use of this device makes it even more cost-effective.

Clearly, many of these advantages can also serve for the optimization, calibration and diagnostics of other standard gas chromatography detectors, including FID, ECD, NPD, FPD, TCD, IRD, SCD, AED, etc.

B. Direct Sample Introduction for GC Analysis

This is a novel approach for GC sampling. In comparison with the conventional syringe-based liquid dispensing, it has several very important advantages and new features.

Very dirty samples can be introduced, including "sludges" such as urine, blood (plasma or serum), solutions with non-volatile compounds, liquified vegetables, fruit or meat (through their blending with acetone, ethylacetate, isopropanol or another solvent), milk, crude oil, etc.

Substantial time and cost is saved through the elimination or reduction of sample clean-up and extraction procedures involved with dirty sample preparation and clean-up. This method is also more environmentally friendly, due to the elimination of harmful extraction solvents such as methylene chloride.

Solid complex small samples can be analyzed, such as bacteria and germs, very small pieces of tissue, hair, etc. These samples will be anlayzed by their thermal extraction. Recently, this method was successfully employed for drug analysis in human hair.

In the analysis of drugs in biofluids such as urine or pesticides in vegetables, fruits and other food items, the method of intra-GG injector—thermal extraction is potentially more uniform in its recovery than liquid or solid phase extraction methods. Since the conflict between the first step of sample extraction by solvent liquification and the consecutive extraction by another solvent is avoided, thermal extraction can provide a more uniform recovery. These problems can be severe when products with a high fat concentration are involved.

The sample size can be substantially reduced due to the elimination of extraction solvents handling requirements. Thus, very small-sized samples can be analyzed. This can be very important in blood analysis of babies, hair analysis for its drug content, etc.

Lower minimum detected concentrations can be realized with conventional extract samples. The sample size of various extracts is generally limited to 1 µL. One of the major reasons for this limitation is that the sample clean-up in the extraction process is incomplete and several undesirable species are not efficiently removed. With the DSI method and device of the present invention, a larger extract sample of 10 µL or more can be injected and analyzed for reduced minimum detected concentration. The analyzed sample amount can be further increased by prior solvent evaporation in a ventilated low temperature oven (such as an old GC) from the removable sample container before its introduction into the GC injector.

The same sample container can be provided with a small amount of derivatization or another chemical reaction agent for the promotion of low volume-effective sample chemical modification, with a minimal amount of chemicals and effort.

While the basic idea is sampling in a removable sample container that is directly introduced into the GC injector, several improvements and variations are considered, depending on the exact application, to further optimize the method of the invention.

The simplest and easiest to obtain sample container is the glass vial or test tube. These test tubes are commercially available in a wide range of suitable sizes, either for melting point determination or for conventional direct sample introduction into mass spectrometer ion sources. These small containers cost 10–25 cents each and are thus disposable. On the other hand, pure quartz test tubes are also commerically available and can be recycled by oven oxidation followed by solvent agitation.

The easiest way to use the DSI is to design it to be inserted into the existing GC injector liners. However, a liner with larger internal diameter will enable the introduction of wider sample containers that are easier to use and to bring the sample into them and can also contain larger sample volumes. Thus, it is easy to realize that for certain applications, the GC liner can be replaced by a wider one and even the whole GC injector can be redesigned for optimal DSI performance.

Figures 2, 3, 4, 5:
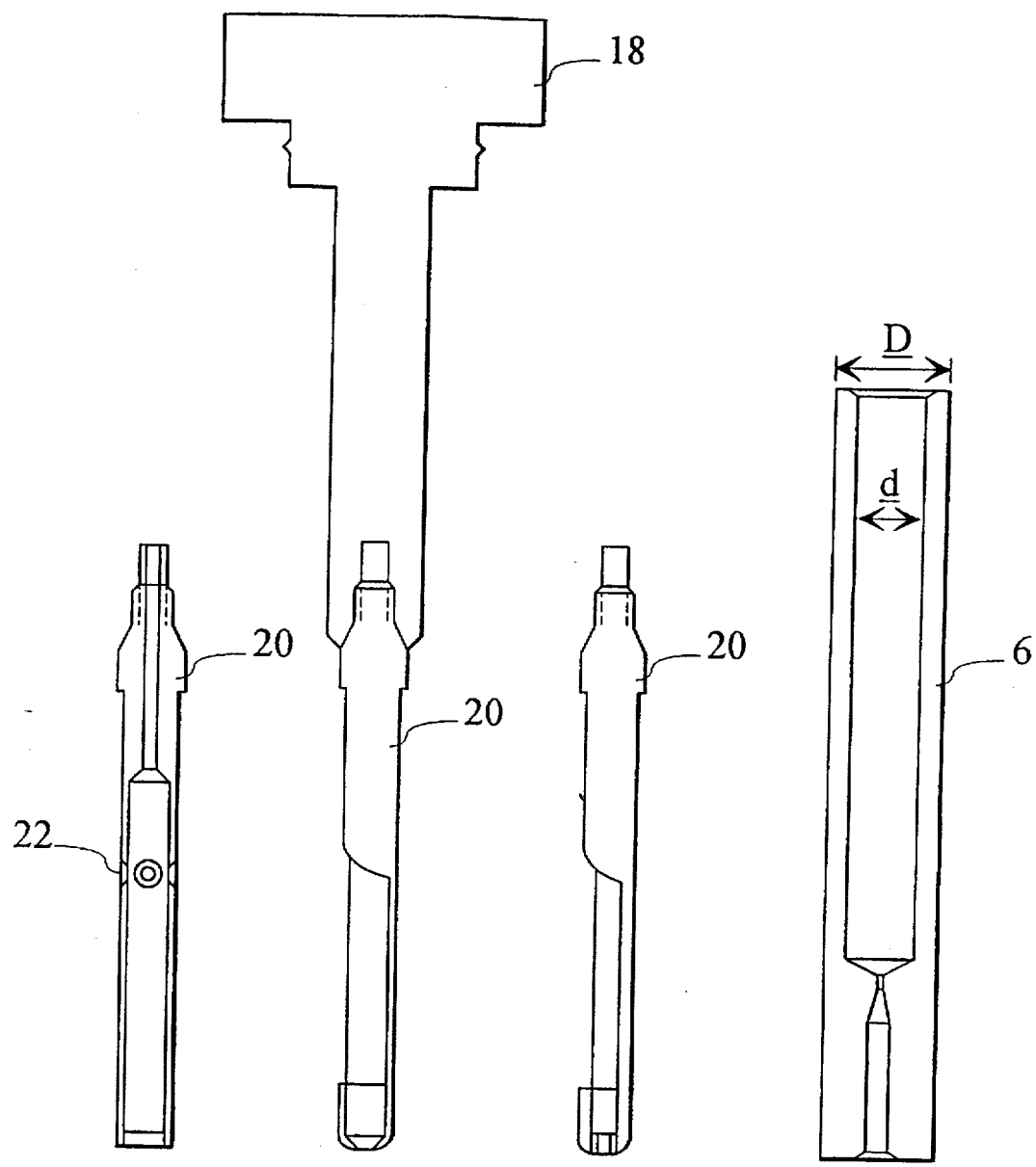
FIG. 2 is a schematic illustration of a liner, modified to possess a relatively wide internal diameter.
FIG. 3 is a schematic illustration of a sample container support unit according to the present invention.
FIG. 4 is a schematic illustration of a sample container support unit and a removable handle coupled thereto.
FIG. 5 is a schematic illustration of a sample container support unit for CI or continuous introduction of a deuterating agent into a MS ion source.

Referring to FIG. 2, there are illustrated such simple modifications to the GC injector, enabled by the use of a VESPEL® (is a registered trademark owned by E.I. DuPont De Nemours and Company for stock shapes made of synthetic resinous plastic materials) liner 6 with a wider internal diameter d of 3.8 mm and outer diameter D of 4.6 mm similar to that of the standard glass liners. It was found that it is useful to divide the sample container holder into two pieces: a handle 18 and an actual sample support unit 20 that is screwed into the handle 1B for easy replacement. Three types of sample container support units are described: an inert VESPEL® removable sample container support unit 20 (FIG. 3) is designed to hold standard glass containers with an OD of 1.6 mm; a stainless steel removable sample container support unit 20 (FIG. 4) is designed to hold bigger size glass vials with a 3 mm OD; and a sample container support unit 20 (FIG. 5) is designed to contain a relatively large volume of solvent for the purpose of continuous introduction of CI or deuterating agent into a mass spectrometer ion source.

While a disposable test tube is seemingly the easiest to use as a removable sample container, the sample insertion unit can be designed to carry the sample and act as a removable sample container by itself. In this case, a larger sample size can be used, at the disadvantage of higher frequency cleaning of the DSI removable device. This method can be practical especially with relatively clean samples such as methanol or deuterated methanol that are constantly introduced into the MS ion source for chemical ionization or deuterium exchange, or for the constant introduction of a mass calibration compound. A very simple, unified removable sample container and its holder can be a long test tube with vaporization holes 22 (FIG. 5) and internal cover. This combination can be made at a low cost as disposable sample containers.

The injector temperature and carrier gas flow rate therethrough, can and should be optimized for this application. GC injectors with both temperature and flow programming capabilities are commerically available today.

For the application of the DSI device for GC sample separation and analysis in time, a conventional capillary GC column can be used, with or without a precolumn to further guard against impurities. On the other hand, when the DSI is used for constant flux sample introduction into a mass spectrometer ion source, the GC column used should preferably be short. A typical example is a 1–2 meter microbore capillary with 100 μm internal diameter and 0.1 μm narrow coating film thickness. The internally coated film can also be eliminated and replaced by pure deactivated quartz, for minimal retention and fastest cleaning time. The carrier gas velocity should be increased to the maximum value permissible by the MS ion source vacuum requirements for faster response time and best handling capability of thermally labile and relatively non-volatile compounds.

The use of a supersonic free jet expansion or a supersonic molecular beam GC-MS interface provides several important advantages in allowing a very high column flow rate that can be 200 times higher than is permitted in a conventional bench top GC-MS. The use of supersonic molecular beam mass spectrometry also provides ultra-fast MS ion source response time that totally eliminates the ion source memory effects due to the "fly through" molecular motion. Thus, switching between DSI and GC-MS can be very fast. The analysis of thermally labile and non-volatile compounds also greatly benefits from the increased relative abundance of molecular weight peak, due to the vibrational supercooling conditions prevailing in supersonic molecular beams.

Typically, the DSI device will remain in the GC injector during the analysis time and the injector will be cooled after the vaporization. If injector temperature programming capability is not available, for some applications the sample container can be taken out after a short vaporization time and the GC injector can be plugged for the initiation of the GC operation. In other applications, the sample container can be heated and then cooled down to a given temperature, followed by a GC analysis with a polar column, and then the sample can be further heated to a higher temperature for the analysis of the less volatile compounds.

The device described in FIG. 1 is designed for manual operation. Today, commercially available GCs have an autosampler option for automatic sample injection and analysis. The method of DSI with a removable sample container can easily be automated in several ways. The simplest way is probably to have several sample container holders that are smaller and without the manual handle, designed for automatic (robotic) insertion and operation, one sample after the other. The automatic operation can be further upgraded also to include automatic sample introduction into the removable sample container and automatic loading of the removable sample container into its holder.

Figure 6:
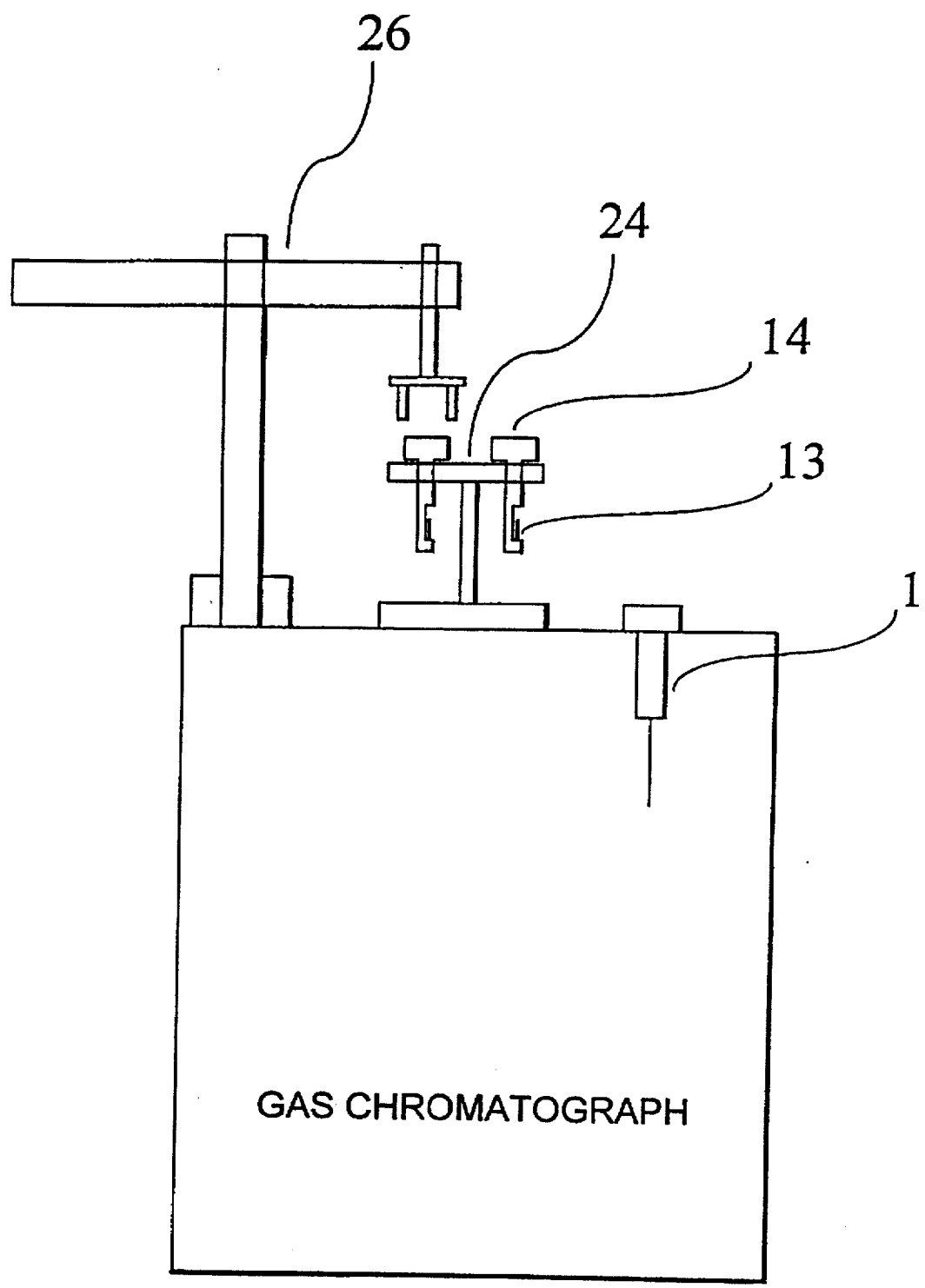
FIG. 6 is a schematic diagram of an automatic sample loading system.

FIG. 6 shows a schematic diagram of an automated version of the DSI with the removable sample container according to the present invention. The removable sample container 13 is placed in its holder 14. Several loaded sample holders (typically 6–60) are located on a carousel 54, as in conventional GC autosamplers. A robot arm 26 can automatically, by means of a computer control, carry a sample container in its holder and introduce it into the gas chromatograph injector 1. The same robot arm 26 also removes the used sample container from the previous analyses in its holder and places it back in the carousel.

The surface quality of the removable sample container and its holder is a very important parameter for achieving good thermal extraction recovery and reproducible results. While the glass or quartz vials can be easily deactivated, the holder standard stainless steel is an active material that can promote adsorption and catalytic dissociation. The stainless steel, however, is usually chosen based on its strength with thin walls. In case a wider injector liner is used, a portion of the sample container holder (or all of it) can be replaced by a high temperature Vespel inert plastic. Alternatively, the stainless steel can be nickel or gold-coated for its passivation, or coated with a special inert high temperature lacquer. Recently, a special very inert fused silica coating process was developed by Restek Corporation, providing very promising, highly inert surfaces that seem ideal for the sample container holder.

It can be easily realized that the DSI method and device of the present invention can be applied to a very broad range of samples, including pure solids, liquids, solutions, dirty sample solutions with residues, sludges, biofluids including urine or blood as is, or processed (serum, plasma, extracts), organ tissues, skin, microorganisms, hair, dirty soil fluids or extracts, and liquid or liquified food products, including fruit, juice, vegetables, spices, meat, milk, etc.

A modification in the removable sample container is the use of an open-ended capillary tube instead of the standard small test tube container or vial. The ideal open-ended capillary is a piece of 5–6 cm long (similar to the length of a GC syringe needle when 5 cm are exposed) standard open tubular column, routinely used for gas chromatography analysis (30 meter long columns). These capillary columns are easily available with a large selection of inner diameters including 50, 75, 100, 150, 180, 200, 220, 250, 320, 530, 750 µm. These capillaries are made of a thin (approximately 50–100 µm) pure fused silica coated by a thin (approximately 20–40 µm) coating of a high temperature Vespel plastic (or aluminum or stainless steel) to eliminate the fused silica fragility. These capillaries can be purchased with a variety of internal adsorption layer coating materials and thicknesses. The most widely used coating is dimethylsiloxane polymer at 0.25–1.5 µm film thickness. These columns are also available as pure uncoated deactivated fused silica for the highest inertness and least adsorption. The capillary size 530 µm ID has 680–730 µm OD and is especially suitable for serving as a disposable removable sample container. Its relatively larger ID provides a relatively high sample capacity of 2 µL per cm, combined with reasonable strength and OD similar to that of standard GC syringes. It was tested to easily penetrate the standard GC septa without breaking. It can also easily be combined with a modified standard GC syringe. It can further be equipped with a small internal plug of glass or quartz wool that can serve as a filter or promote gentler solvent vaporization.

Figures 7, 8:
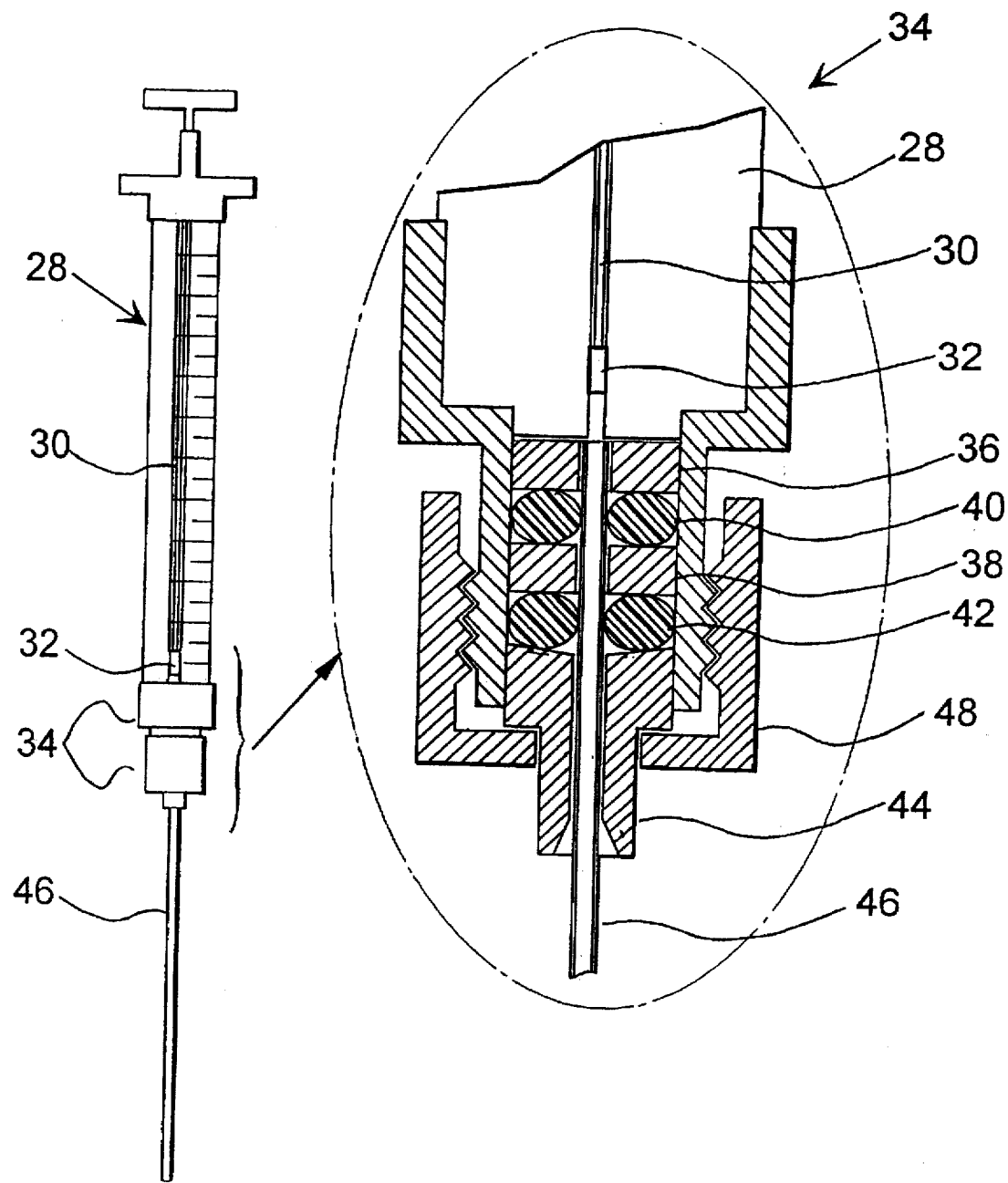
FIG. 7 is a side view of a syringe modified to hold a capillary functioning as a sample container.
FIG. 8 is a cross-sectional view of a portion of the syringe of FIG. 7, showing details of the capillary gripping structure.

In FIGS. 7 and 8 there is shown such a modified syringe, adapted for the easy acceptance and removal of pieces of 6 cm long, 0.68 mm OD, 0.53 mm ID, standard GC capillaries known as "megabore". The syringe 28 contains a plunger 30, preferably with a teflon seal 32 at its lower end and a needle house 34. The needle house contains two needle guides 36, 38 that also act as bases for the Viton O-ring seals 40, 42. The needle guide 44 also serves to clamp and press the two O-rings for an easy sealing combined with a positive grip holding on the capillary tube 46. The clamp 48 enables positive sealing and capillary gripping by a half of a turn and releases the capillary with a half a turn back for easy removal.

In this unique device, the syringe body serves for the dual purposes both of loading the removable sample container with a precisely known liquid amount and serving as a removable sample container holder during its introduction into the GC injector. Unlike the DSI described with reference to FIG. 1, no special GC injector-sample container holder adaptor is required.

Figure 9:
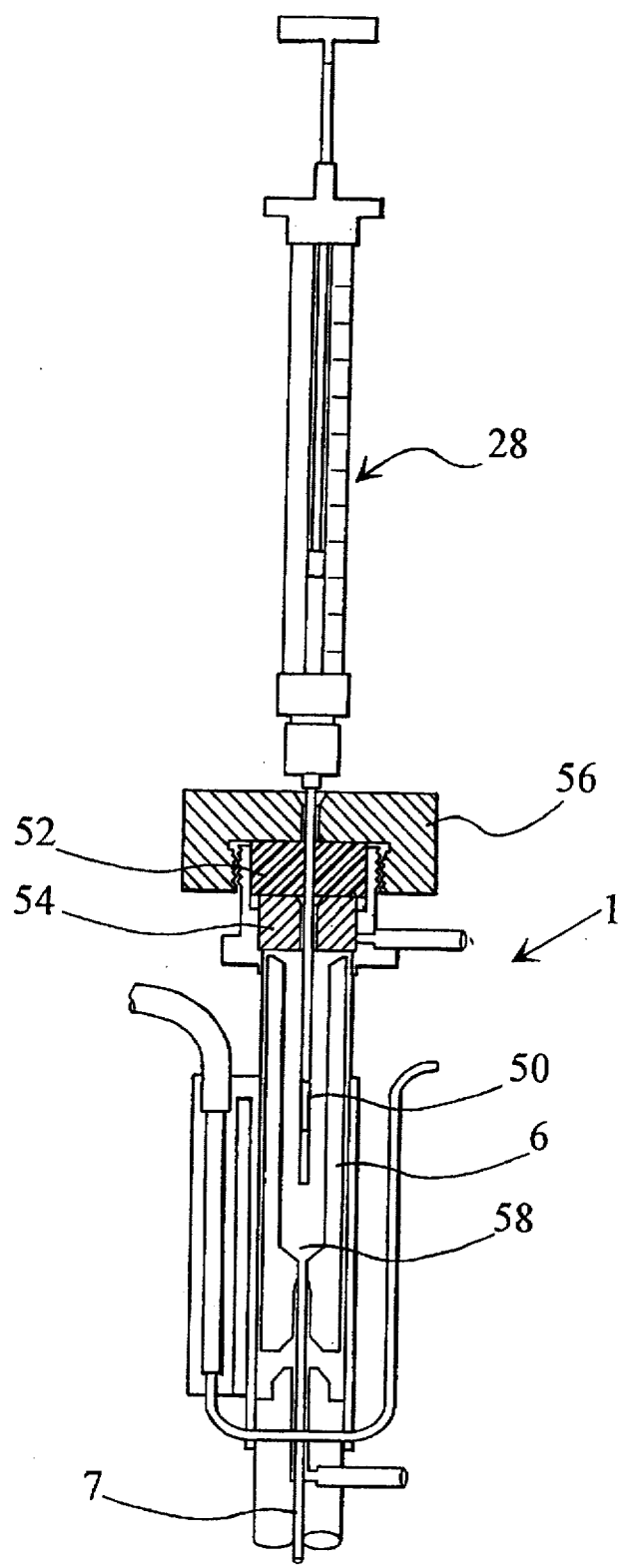
FIG. 9 is a side and partial cross-sectional view of the device of FIGS. 7 and 8, as introduced into a GC injector.

In FIG. 9, there is shown the syringe 28 of FIG. 7, fitted with the capillary container 46 introduced in the GC injector 1. The capillary sample container 46 containing sample 50 is introduced into the GC through the standard septum seal 52 pressed against the septum seat 54 by means of a septum clamp 56. The syringe 28 holds the capillary sample container 46, loaded with the sample 50, above the entrance 58 to the analytical column 7. The sample 50 is not dispensed as usual, but in contrast it is held for a few seconds, as shown, to enable sample vaporization while leaving the deposit inside the capillary.

A preferred method of operation of this open-ended capillary removable sample container includes the following steps:

1. A 6 cm long clean capillary is first installed into the syringe, as shown in FIGS. 7, 8 and 9.

2. The capillary container 46 is inserted into a liquid sample and the syringe plunger 30 is pulled up to fill the capillary container with the required sample volume.

3. The capillary container 46 is pulled out from the liquid sample and the plunger is further pulled up, so that the sample plug is moved about 1–3 cm from the end of the capillary.

4. The syringe with the sample 50 in the capillary is brought to the GC and the capillary is introduced into the GC injector 1 through the standard septum seal 52.

5. The GC injector is maintained at a relatively low temperature that is compatible with gentle vaporization of the sample solvent that is maintained inside the capillary. The syringe plunger is not depressed, to avoid any dispensing of the dirty sample into the GC injector. The plunger serves as an upper seal, thereby avoiding upward gas and sample leakage.

6. After a predetermined time when the solvent was vaporized, the GC injector temperature is raised to the usual high temperature that is required for the vaporization of the sample compounds to be analyzed, while the GC analysis column is at a low temperature for the cryo-focusing of these compounds.

7. After an additional predetermined time, the capillary is removed from the injector, together with all the unvaporized dirty sample residue and the GC analysis temperature program begins as usual.

8. The dirty used capillary is removed from the syringe and can be disposed of, and a new capillary is loaded with another sample for the next analysis.

The GC injector temperature can also be maintained at its standard high temperature for faster vaporization and, in this case, while most of the dirt residue will remain inside the capillary, some residue can be swept with the spray that is formed at this higher temperature in cases where a limited amount of residue inside the injector lines can be tolerated. The sample plug can be placed further up inside the capillary for achieving a better protection against such residue sweeping out.

One of the major questions involved in this method of injection is the mechanism of vaporization, since no carrier gas is sweeping the interior of the sample capillary. While a substantial portion of the vaporized sample compounds are carried to the injector liner by diffusion, the temperature increase at the upper portion of the capillary induces gas expansion that further sweeps out the sample compounds. The actual sample sweeping process is also affected by the high pressure and temperature conditions inside the GC injector that can "push" the sample solvent plug before and during its evaporation. When a complete intra-capillary vapour sweeping is required, a simple solution is provided by the addition of an upper solvent plug. Accordingly, before the sample loading, a small amount of solvent (i.e., 0.5 µL) is loaded and then 2–4 µL of air are loaded by further moving up the plunger before the sample loading. Using this method, a small amount of solvent is found above the sample at a relatively cool portion of the capillary. The slow vaporization of this solvent enables a constant flow of sweeping solvent vapour. Care should be exercised to choose a solvent that will not fully vaporize and will push out the sample plug before the vaporization of its solvent.

An effective protection of the liner and column is provided by the placement of a sample about 1–2 cm away from the end of the capillary. This positioning enables protection due to further adsorption trapping of 1–2 cm of column of very low volatility compounds or of a spray of small liquid droplets. In a case where even a trace of sample dirt that is adsorbed on the column edge is considered harmful, the sample can be further pumped upward and then the capillary can be taken out and inverted. In this way, the insertion of a clean capillary edge is ensured.

A very appealing additional feature of the open ended capillary sample container pertains to the nature and kind of internal coating used. For a large variety of samples, the use of a pure clean internal quartz surface, with or without surface deactivation, is the most desirable solution since it enables the easiest vaporization and acts as an internal "retention gap". On the other hand, the use of internal adsorption coating as in standard GC columns, possesses several distinctive advantages:

The coating material can be chosen to deplete and reduce the vaporization of interfering compounds, and in this way, act as a crude GC—GC pre-separation step. For example, a polar coating can be used for the reduced vaporization of polar compounds.

The coating material can be used for solid phase extraction. In the simplest way, this solid phase extraction is achieved by loading the sample for some time, a few seconds up to a few minutes, to allow the adsorption of the sample compounds on the internal capillary surface. The sample solvent is then pushed out and the sample adsorbed in the capillary is introduced for analysis as before, but with a much smaller amount of solvent and its dirty residue inside. The effectiveness of this intra-capillary solid phase extraction can be further increased by repetitive sample loading into the capillary, so that every predetermined time such as one minute, the previous sample is discharged back or to a waste container and a new sample is loaded. Depending on the partition of the sample compounds between the solid adsorption coating and liquid solvent, an effective extraction of the sample compounds from a relatively large solvent volume can be achieved.

A simple, yet effective method to achieve sample extraction from a large solution volume is through the slow pumping of a given volume of the solution through the capillary, and then loading the capillary on its "syringe" holder for introduction into the GC as before.

To further clean the capillary before introduction, the capillary can even be washed from the inside by clean water or another solvent that does not dissolve the analyzed sample compounds. In order to evaluate this approach, the syringe shown in FIG. 7 was cut and installed into a Wilson seal, which was connected through a buffer chamber and a frit flow restrictor to a small pump. The use of a short piece of capillary column is characterized by several distinctive advantages:

Capillary columns are widely used and are thus massproduced and sold at a price of under $15/meter. These short capillaries should be available at about $1 each and can be used as disposable containers. The capillaries can even be cut at the laboratory from existing standard GC capillaries.

The capillary has a much larger (1000 times) ratio of surface area to internal volume and diameter than that of a fiber rod immersed in a 1 ml solution vial. Thus, the adsorption kinetics are much faster.

The method of solution pumping through the capillary is unique to the use of a capillary.

A very broad range of capillary coatings (and sizes) are available to enable optimal choice of selective extraction to non-polar, polar and even chiral compounds. A broad temperature range can also be employed, as columns of carboxysiloxane are available with an operation temperature range up to 480° C., i.e., above the maximum common GC injector temperatures.

The methods and devices hereinbefore described have been experimentally tested, studied and evaluated in terms of optimal operation conditions and performance. In FIG. 10, there is illustrated the use of the DSI for direct sampling into a mass spectrometer. The GC-MS used is based on a standard commercial GC model Star CX of VARIAN® (Varian is a registered trademark owned by Varian Associates, Inc.), interfaced with a supersonic molecular beam into a quadrupole mass spectrometer. The gas chromatograph was equipped with a temperature programmable injector connected to the supersonic nozzle interface, with a 3-meter long capillary column having 0.53 mm ID.

Figure 10A:
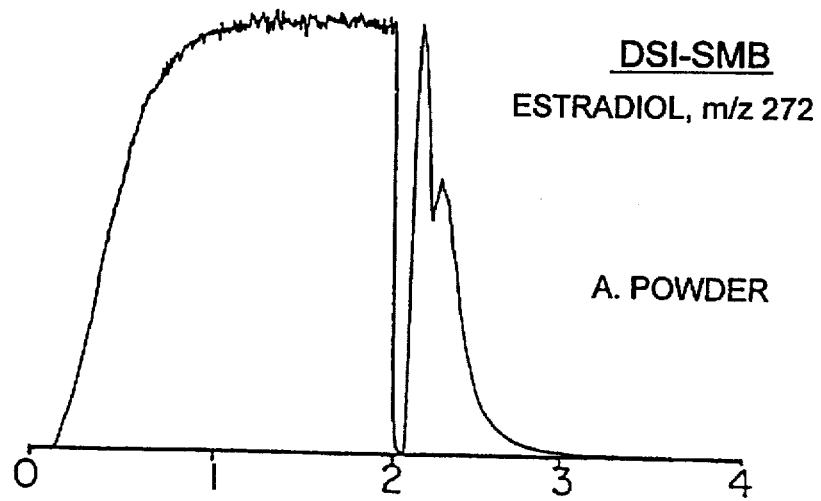
FIGS. 10A, 10B and 10C show gas chromatograms of a powder (FIG. 10A), a first solution (FIG. 10B) and a second solution (FIG. 10C) as obtained by a MS fed by a sample introduced therein by the device of FIG. 1.

In FIG. 10, there are shown typical results of three modes of operation. The trace of FIG. 10A describes the flux of 17β-estradiol at the mass spectrometer versus time, when the sample compound was introduced as a powder in a test tube, as shown in FIG. 1. 17β-estradiol is a thermally labile and polar compound that usually requires derivatization for GC analysis and thus, as a pure sample, its DSI sampling is the preferred analysis method. The GC injector temperature was 220° C., and the column temperature was 280° C. with a 50 ml/min helium column flow rate. Under these conditions, the 17β-estradiol signal appeared after a few seconds and reached a steady state flux in less than one minute. This period was probably determined by the heat capacity of the sample container and its holder. This is a much faster response in comparison with standard DSI devices. After 2 minutes, the sample container was removed and when the injector was open, the signal dropped to zero. When the injector was closed again with the empty sample holder, the signal showed fast cleaning kinetics, with a small spike due to a change in the holder position. In contrast to a standard DSI device, the trace of FIG. 10A shows a complete cycle of sampling and cleaning in under 4 minutes.

Figure 10B:
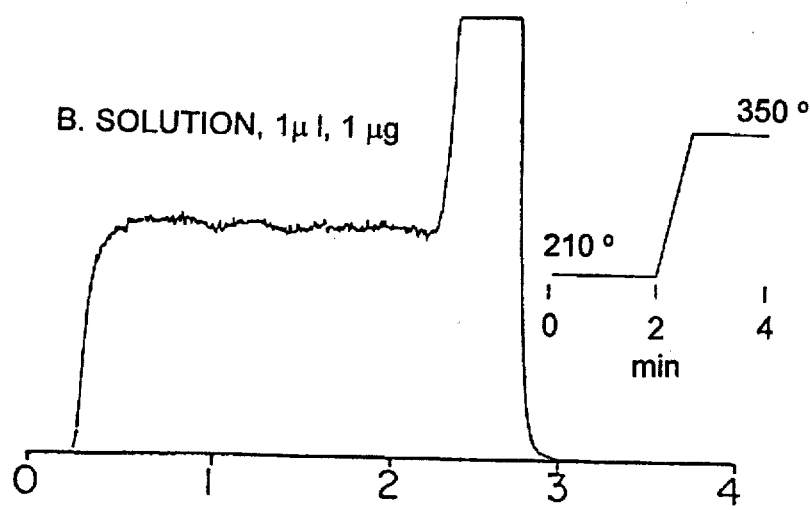

In the trace of FIG. 10B, a solution of 1 μL of methanol containing 1 microgram of 17β-estradiol was sampled. In this case, the sample loading time into the vial was faster and simpler with a standard liquid dispensing syringe. Again, at 220° C. injector temperature, a solvent vaporization and steady state sampling was achieved in less than 30 seconds. After 2 minutes a time-programmed cleaning was performed by heating the injector to 350° C., and the 17β-estradiol signal was increased momentarily until it was fully evaporated and quickly self-cleaned, becoming ready for a new sample loading in the same or another vial. The steady signal achieved for a few minutes with a flux of about 4 nanogram/ sec is very useful for mass spectrometry studies.

Figure 10C:
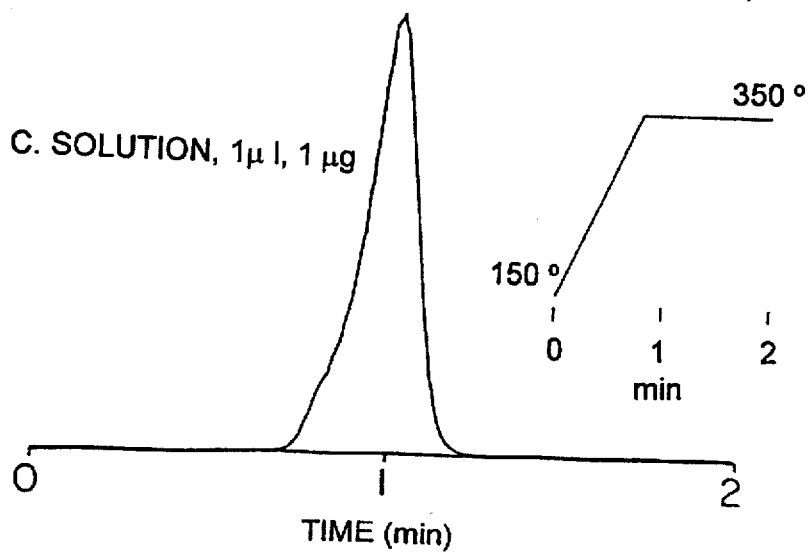

In the trace of FIG. 10C, the sample was introduced at an injector temperature of 150° C. that was ramped to 320° C. at a rate of 150° C./min. The 17β-estradiol flux is characterized by a peak in its time dependence of about 8 seconds width and a rather high flux (over 100 ng/sec). In this case, the DSI showed an additional time separation dimension of a single stage distillation, in addition to a high signal flux and fast self-cleaning, combined with a universal response to a large group of compounds.

Figure 11:
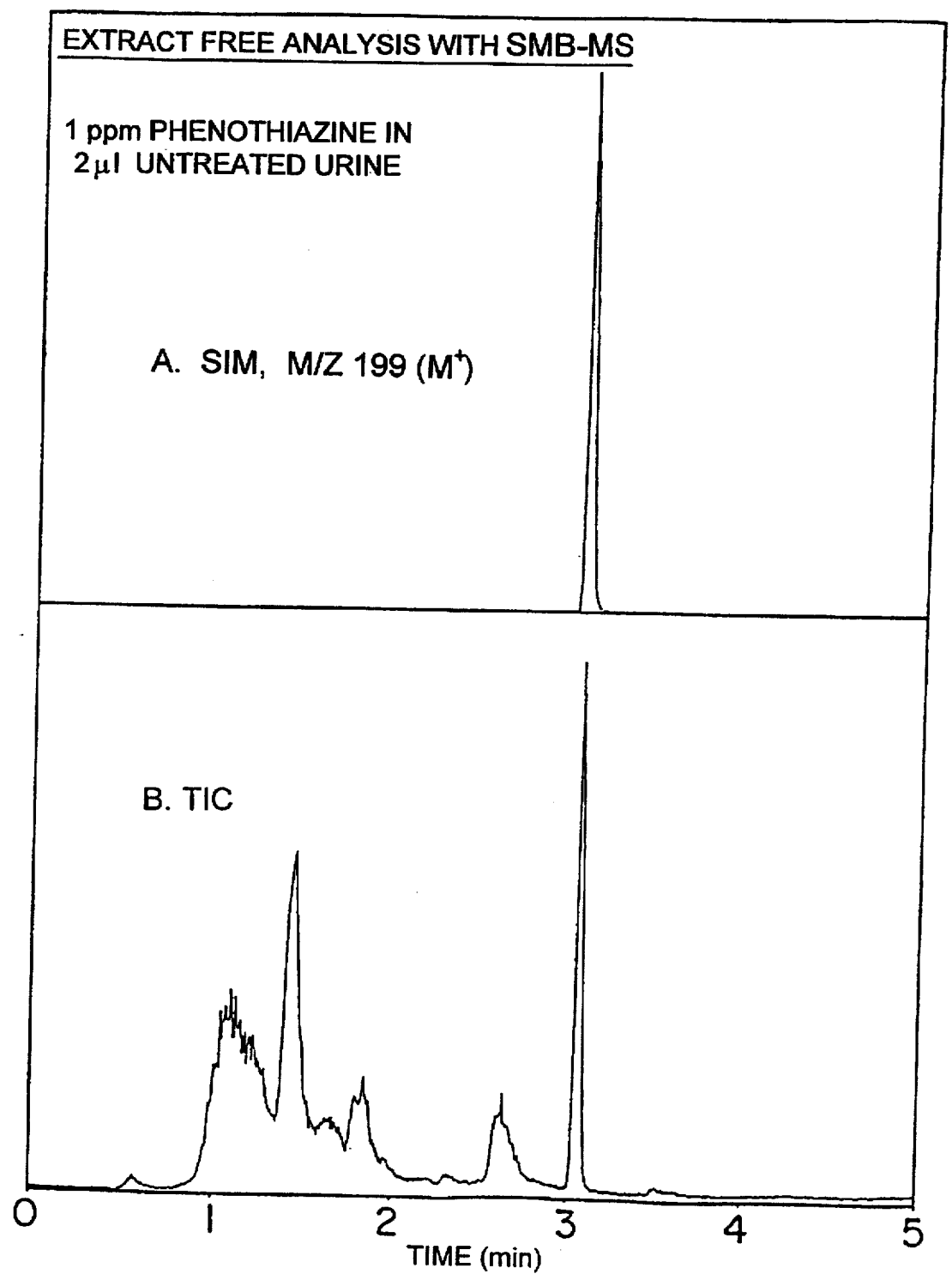
FIG. 11 shows a GC-MS analysis of a drug in human urine as obtained by utilizing the device of FIG. 1.

In FIG. 11, the same DSI device and column employed in FIG. 10 was used for standard gas chromatographic analysis of phenothiazine drug in human urine. 2 μL urine, spiked with 1 ppm phenothiazine, were loaded with a syringe into the removable sample test tube. The test tube was introduced into the GC injector and maintained at 120° C. for 0.5 minutes, for gentle water vaporization. After 0.5 minutes, the injector temperature was raised to 230° C. at a rate of 300° C./min, and then immediately cooled back to 120° C. The GC column temperature was held at 80° C. for 1 minute and then programmed up to 280° C. at a rate of 50° C./min. The column flow rate was 20 ml/min. Most important is the fact that FIG. 11 demonstrates the analysis of a drug in unprocessed urine that was sampled as is, without any extraction or sample processing. Yet a very clean and informative GC-MS trace is observed with a clear phenothiazine peak at the lower total ion count chromatogram. A computer-reconstructed single ion monitoring trace at the molecular ion (m/z 199) reveals a single GC peak of phenothiazine that is characterized by a signal-to-noise ratio approaching $10^4$. Thus, sub ppb levels of drugs in urine can be analyzed by GC-MS without sample preparation. The other peaks are of unidentified natural compounds, except the peak at 2.7 min that was identified to be of caffeine. Even after many dozens of such sample introductions, no dirt was visually observed on the GC liner and the performance remained unchanged. The removable sample container always showed a brown spot at its bottom of salt and unidentified organic residue deposit. While the majority of this residue was at the bottom, some of it migrated a few millimeters upwards. It was concluded by visual observation that 12–15 mm long vials, with 1.6 mm OD and 1.2 mm ID, were enough to contain the vast majority of the residue, combined with an effective thermal extraction of the semi-volatile compounds.

The DSI was also studied in the analysis of pesticides in fruit, vegetables, meat and milk. In this study, the detector used was a pulsed flame photometric detector (PFPD), i.e. a selective detector for the presence of phosphorus pesticides which can also selectively detect sulfur compounds. A 6 meter long capillary column with 0.25 mm ID was used with a 5 ml/min helium column flow rate that is desirable for good thermal extraction of the pesticides from the test tube. This flow rate is above the optimal flow rate for GC separation.

Figure 12:
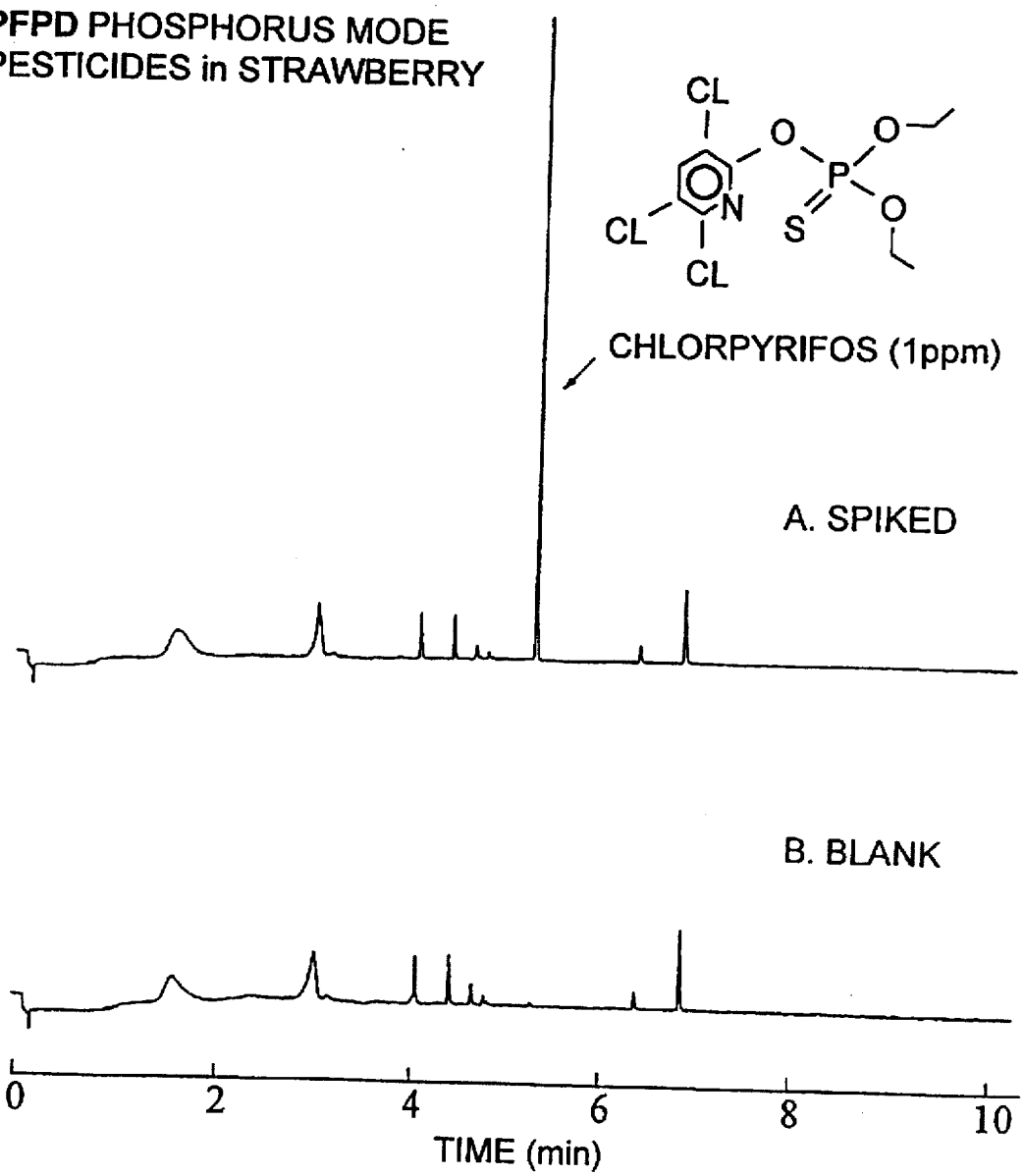
FIG. 12 is a gas chromatogram of a phosphorous pesticide in a strawberry, as performed with the device of FIG. 1.

In FIG. 12 there is shown the analysis of phosphorus pesticide in strawberries. 105 g of strawberries were mixed with 210 ml acetone and blended for 3 minutes. One µL of the resulting thick liquid of acetone-blended strawberry was loaded into the removable sample container vial (15 mm long, 16 mm OD, 1.2 mm ID), and it was introduced into the GC. The GC injector temperature was maintained at 120° C. for solvent vaporization and after 1 minute it was ramped to 240° C. at a 120° C./min injector temperature programming rate. The column was at 50° C. for pesticides cryo-trapping and after 2 minutes, it was temperature-programmed to 280° C. at 40° C./min.

In FIG. 12, the lower trace shows the naturally occurring organophosphorus and pesticides compounds found. The upper chromatogram was obtained by the spiking of the blended strawberry sample with 0.33 ppm (weight) chlorpyrifos that reflects about 1 ppm (weight) in the unblended strawberries. A clear signal of chlorpyrifos pesticide is observed that can be used for the calibration of the other pesticides.

Figure 13:
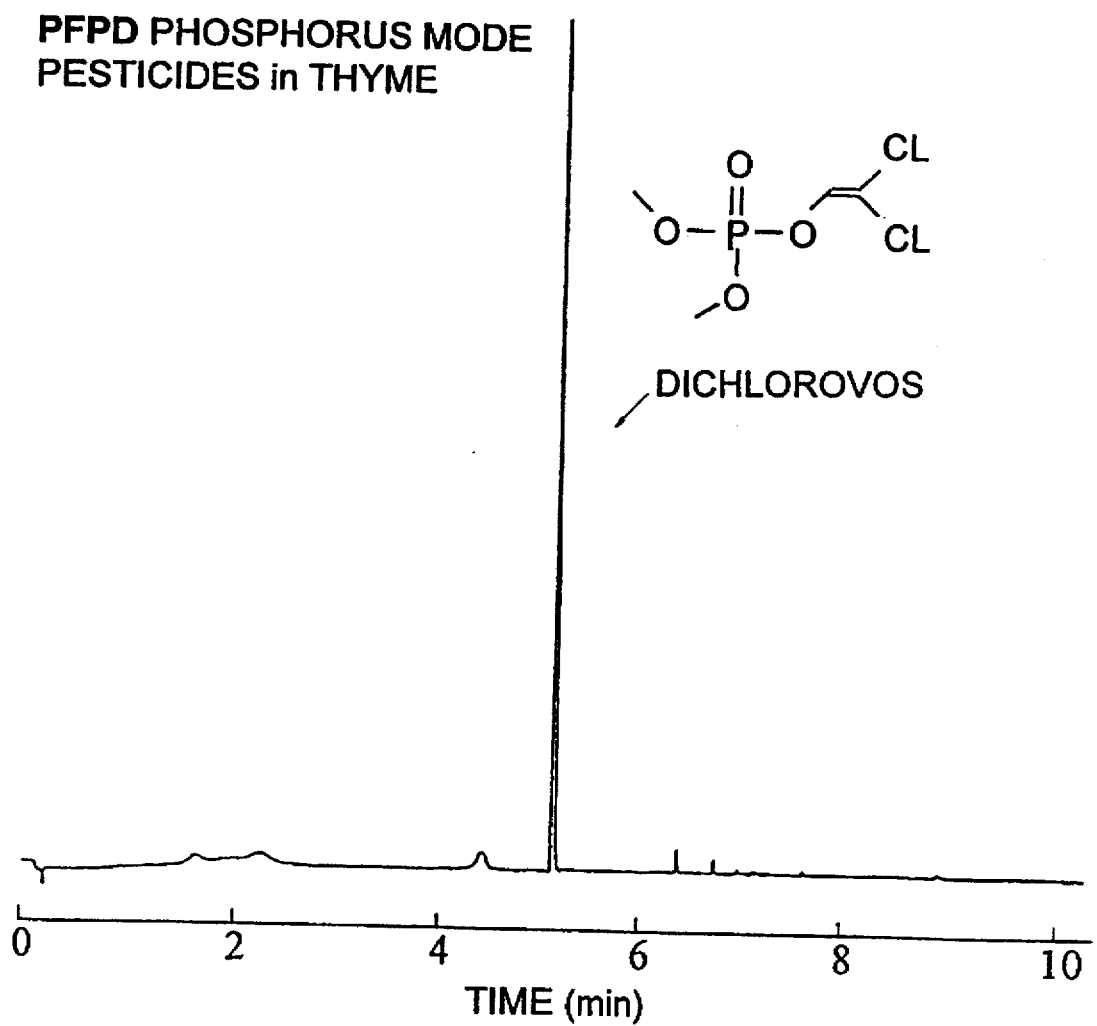
FIG. 13 is a gas chromatogram of a sample of thyme performed with the device of FIG. 1.

In FIG. 13, there is demonstrated an analysis of a real sample of thyme (spice) that was found, by standard methods employing an extraction procedure, to contain 1.4 ppm dichlorovos pesticide. Here again, as in FIG. 12, extract-free sampling was employed using the DSI device of FIG. 1, with a blended only sample at similar conditions to those described with reference to FIG. 12.

Figure 14:
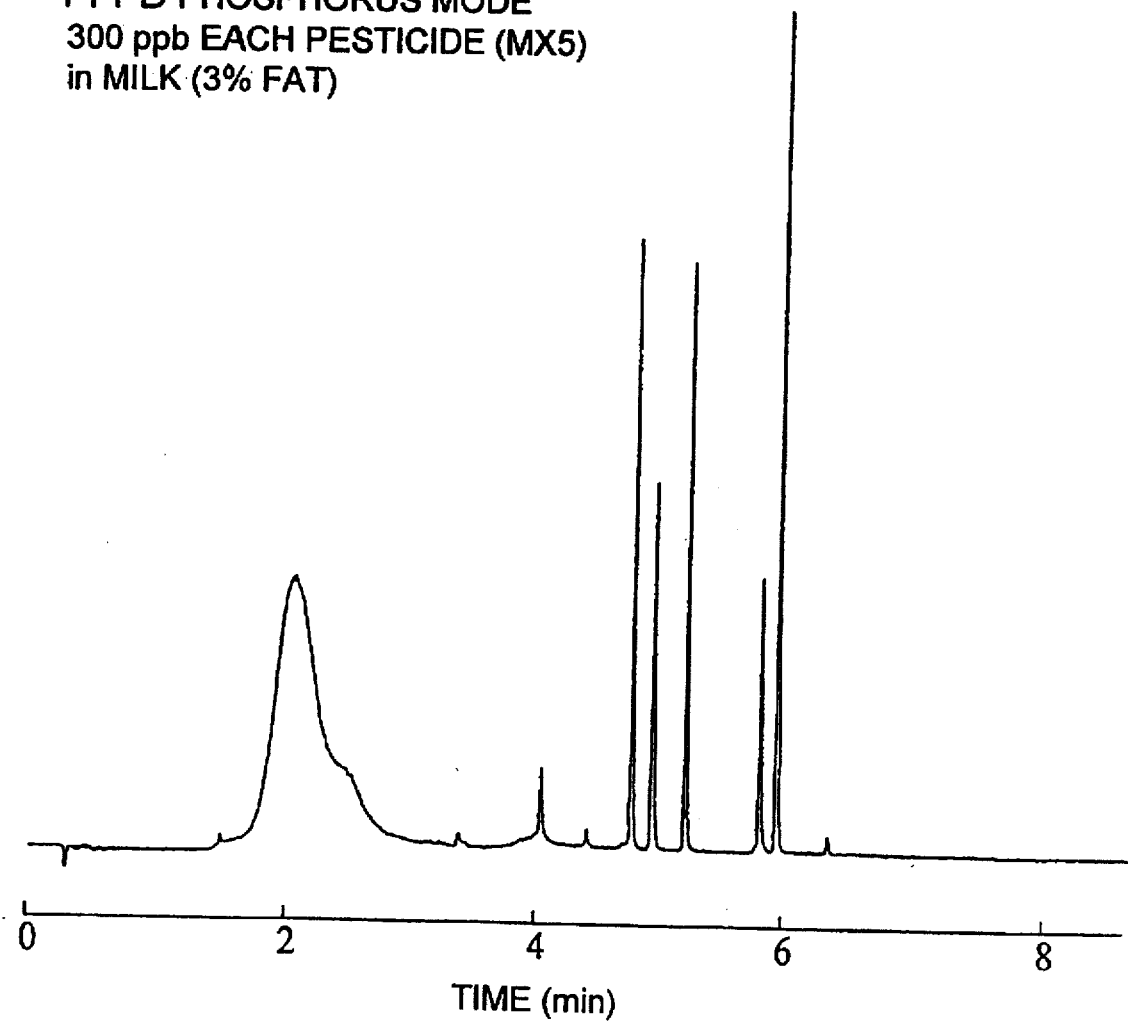
FIG. 14 is a gas chromatogram of milk spiked with five pesticides, performed with the device of FIG. 1.

In FIG. 14, there is shown the analysis of milk with 3% fat content. The milk was spiked with 300 ppb (weight) each of the pesticides diazinon, methylparathion, parathion, methyltrithion and ethion. The milk was introduced into the sample vial without any sample preparation. 1 µL milk was placed together with an additional 1 µL water. The GC injector and oven conditions were as described above with reference to FIG. 12. All five pesticides are clearly observed with close to uniform response as evaluated, based on their relative phosphorus content. The two smaller early eluting peaks are naturally-occurring unidentified organophosphorous compounds, while the broad early peak is due to an unidentified sulfur-containing compound.

The analysis of milk resulted in a thick brown-black deposit of "burnt" milk, fully contained in the vial, which had to be disposed of after the analysis. Similarly, the thyme and strawberry samples left a green and yellow/orange stain in the used vial. No dirt was visually observed in the GC liner. It is also noted that the chromatograms of FIGS. 10–14 were achieved with a removable sample container holder made from stainless steel 316, coated with a high-temperature lacquer that is usually used as a leak sealant in high vacuum systems.

Figure 15:
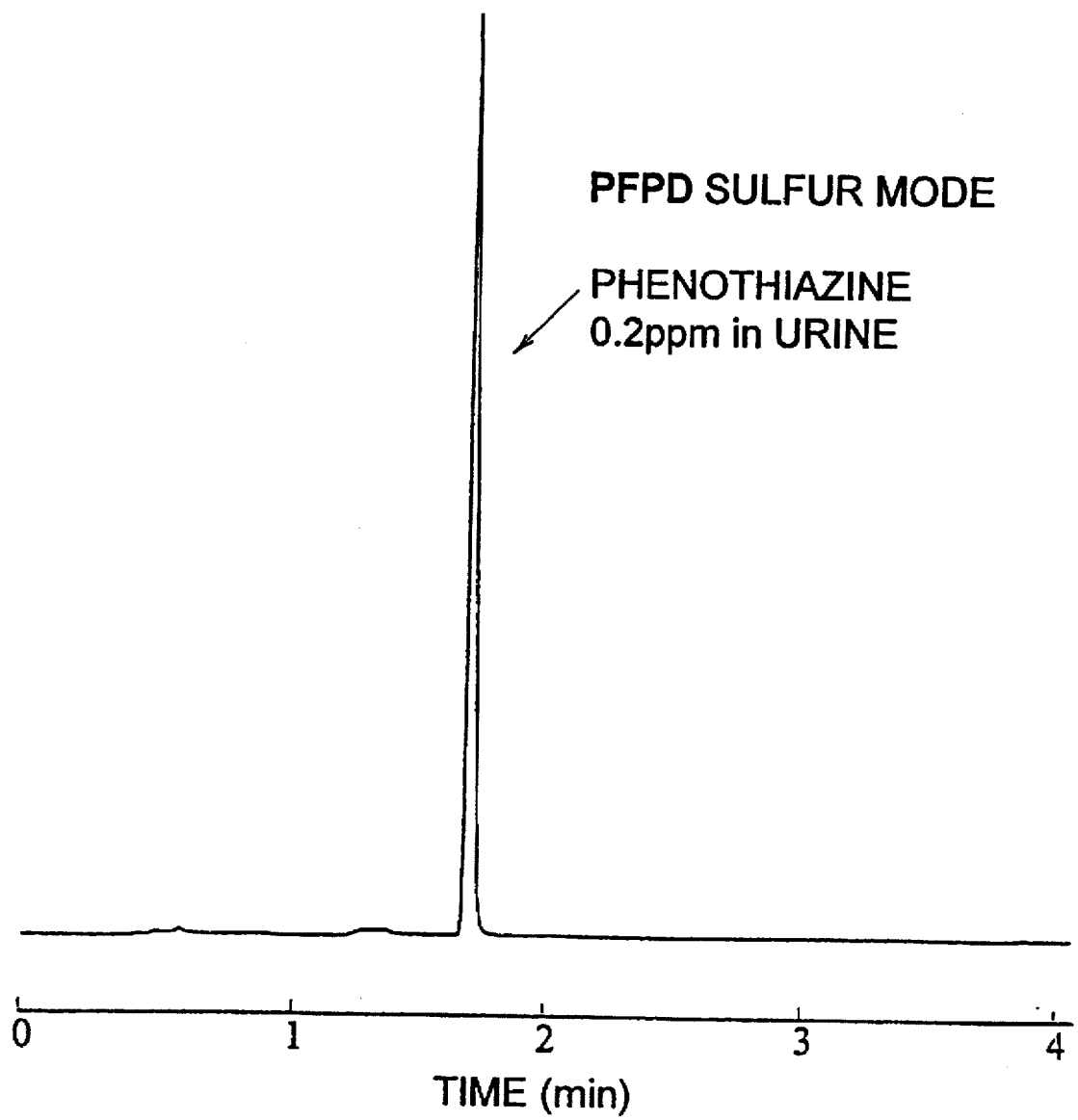
FIG. 15 is a gas chromatogram of phenothiazine drug in urine, using an open-ended capillary sample container and a syringe holder as illustrated in FIG. 9.

FIG. 15 demonstrates the analysis of 200 ppb (weight) phenothiazine drug in urine, using the open-ended capillary sample container and its syringe holder as described in FIGS. 7–9. A 6 cm long column with 0.53 mm ID and 0.68 mm OD was used, with a 1.5 µ internal film coating of dimethylsilicon (DB-1 of J & W). The sample loading was achieved by loading 6 µL urine, waiting for a time period of 30 seconds, followed by discharge of the urine and loading another 6 µL urine sample 5 repetitive times. After 5 loadings of 6 µL urine samples, the empty column contained the internally adsorbed drugs and other compounds on its internal adsorption thin layer. The capillary was then introduced into the GC injector, maintained at 250° C. in the usual way through a pre-penetrated standard septum, and held inside for vaporization for 12 seconds before its removal.

The used capillary was discarded after each analysis. FIG. 15 demonstrates enhanced sensitivity using this method, due to the relatively large urine sample probed, yet with relatively small perturbations. By comparison to the signal level obtained using the sample vial and DSI as described in FIG. 1, it was concluded that the adsorption efficiency was about 30% and it depended upon the time of equilibration up to at least 1 minute.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for sample introduction into a gas chromatograph for performing sample analysis, comprising:
   introducing a sample into a removable sample container;
   placing said container in a sample introduction device;
   inserting said device with said container into a gas chromatograph injector;
   vaporizing the sample in the gas chromatograph injector for effecting analysis of said sample;

sweeping said vaporized sample through a column by a carrier gas, and detecting said sample with a detector connected to the gas chromatograph through said column.

2. The method according to claim 1, wherein said detector is a mass spectrometer.

3. The method according to claim 1, wherein said gas chromatograph injector and said column are heated to temperatures sufficient to vaporize said sample to produce a flow of compounds which are swept to said detector by said carrier gas at a rate which enables the continuous analysis of said sample by said detector.

4. The method according to claim 1, wherein the vaporized sample is swept by a carrier gas through said gas chromatograph injector into a column while causing non-volatile residues of said sample to be retained in said sample container.

5. The method according to claim 1, wherein said column serves as a transfer line for the transfer of said sample from said gas chromatograph injector to said detector without sample separation in time.

6. The method according to claim 1, wherein said sample is vaporized and introduced into the gas chromatograph column for its separation in time.

7. The method according to claim 5, wherein said column is a capillary column.

8. The method according to claim 6, wherein said gas chromatograph column is a capillary column.

9. The method according to claim 1, wherein the injector of said gas chromatograph is also alternatively used for conventional syringe-based solvent dispensing sample injection.

10. The method according to claim 1, wherein said sample container is a disposable test tube or vial.

11. The method according to claim 1, wherein said container is recyclable.

12. The method according to claim 10, where said test tube is placed with its sample entrance facing upwards.

13. The method according to claim 1, wherein said sample container is an open-ended capillary.

14. The method according to claim 1, wherein said gas chromatograph injector is a standard injector adjusted to accept a sample container of a large size.

15. The method according to claim 1, further comprising the step of introducing into said container an additional material, to promote a desirable internal chemical reaction such as derivatization.

16. The method according to claim 1, wherein said sample material is dissolved in a solvent and said solvent is evaporated from said removable sample container before its introduction into the injector.

17. The method according to claim 1, wherein the temperature of said gas chromatograph injector is kept constant or time programmed.

18. The method according to claim 1, wherein the carrier gas flow rate through said gas chromatograph injector and column is kept constant or time programmed.

19. The method according to claim 1, wherein a carrier gas propelled through the gas chromatograph injector substantially enter the column of said chromatograph in its entirety.

20. The method according to claim 1, wherein a carrier gas propelled through the gas chromatograph injector is split in a time-programmed manner, prior to its entering said column.

21. The method according to claim 2, wherein said gas chromatograph is interfaced with said mass spectrometer detector through a high gas flow rate supersonic expansion.

22. The method according to claim 1, wherein said sample container is removed after the sample vaporization and the injector is plugged, prior to performing analysis.

23. The method according to claim 1, wherein said sample introduction device is removed without said sample container, prior to performing the analysis.

24. The method according to claim 1, wherein said sample container is removed at the termination of the analysis.

25. The method according to claim 1, wherein said sample introduction device is manually manipulated and introduced into the gas chromatograph injector.

26. The method according to claim 1, wherein said sample introduction device with said container is introduced and/or removed by an automated autosampler.

27. The method according to claim 1, wherein said sample is carried in a removable open-ended capillary sample container and introduced into the gas chromatograph injector through its septum or another inlet, without performing liquid injection.

28. The method according to claim 27, wherein said capillary sample container is removably mounted on a syringe serving to retain said sample and to suck a measured amount of sample into said capillary.

29. The method according to claim 27, wherein said capillary sample container is inverted relative to its sample loading end from its orientation when mounted in a syringe or another holder, before introduction into the gas chromatograph.

30. The method according to claim 1, wherein said sample is a solution in a container and said solution is slowly pumped into another solution container through an open-ended capillary sample container.

31. A method employing a device for sample introduction into a gas chromatograph for analyzing said sample in accordance with the method of claim 1, comprising:
    means for coupling a sample introduction device, having means for carrying a removable sample container into a gas chromatography injector;
    means for sealing the sample introduction device and said means for coupling to each other;
    means for vaporizing the sample for affecting its analysis;
    means for transferring vapor of said sample by sweeping it with a carrier gas into a detector, and
    detector means for the detection of said sample.

32. The method as claimed in claim 31, further comprising means for removing said sample container prior to performing the next analysis.

33. The method according to claim 31, wherein said injector and means for vaporizing said sample is a standard gas chromatograph injector also usable for conventional syringe-based solvent dispensing sample injection.

34. The method according to claim 31, wherein said detector means is a mass spectrometer.

35. The method according to claim 31, wherein said detector is a standard detector, for the optimization and/or calibration of the response of that detector.

36. The method according to claim 31, wherein said means for carrying a removable sample container is a needle-like syringe like means for pumping a measurable amount of sample, that further includes means for coupling and removing an open-ended capillary that serves as a removable sample container, and means for retaining said sample in its container while inserted into the gas chromatograph injector.

37. The method according to claim 31, wherein said sample container is equipped with a glass or quartz wool filter.

38. The method according to claim 31, wherein said gas chromatograph includes a capillary column as the means for transferring the vapor of said sample, and said capillary column is short, for achieving a shorter response time and a faster analysis.

39. The method according to claim 31, wherein said material of which said sample introduction device is made, is passivated or coated with fused silica for surface deactivation.

40. The method according to claim 31, wherein said removable sample container is a small glass or quartz test tube vial.

41. The method according to claim 31, wherein said sample container is made of a section of a standard open tubular fused silica capillary column, coated outside with a thin layer as used for gas chromatography transfer lines and without inside adsorption layer coating.

42. The method according to claim 31, wherein, said sample container is made of a section of a standard open tubular fused silica capillary column, coated outside with a thin layer of plastic or metal used for gas chromatography separation, and with a selection of internal surface coating with adsorbing materials.

* * * * *